United States Patent
Matheny

(10) Patent No.: US 9,681,937 B2
(45) Date of Patent: *Jun. 20, 2017

(54) EXTRACELLULAR MATRIX CONSTRUCTS FOR TREATING DAMAGED BIOLOGICAL TISSUE

(71) Applicant: CorMartix-Cardiovascular, Inc., Roswell, GA (US)

(72) Inventor: Robert G Matheny, Norcross, GA (US)

(73) Assignee: CORMATRIX CARDIOVASCULAR, INC., Roswell, GA (US)

(*) Notice: Subject to any disclaimer, the term of this patent is extended or adjusted under 35 U.S.C. 154(b) by 13 days.

This patent is subject to a terminal disclaimer.

(21) Appl. No.: 14/832,017

(22) Filed: Aug. 21, 2015

(65) Prior Publication Data

US 2015/0359622 A1     Dec. 17, 2015

Related U.S. Application Data

(60) Division of application No. 14/155,496, filed on Jan. 15, 2014, now Pat. No. 9,149,496, and a (Continued)

(51) Int. Cl.
| | |
|---|---|
| *A61F 2/02* | (2006.01) |
| *A61F 2/06* | (2013.01) |
| *A61K 38/18* | (2006.01) |
| *A61K 35/12* | (2015.01) |
| *A61L 27/36* | (2006.01) |
| *A61L 27/50* | (2006.01) |

(Continued)

(52) U.S. Cl.
CPC ............ *A61F 2/02* (2013.01); *A61B 17/0057* (2013.01); *A61F 2/848* (2013.01); *A61K 35/12* (2013.01); *A61K 38/18* (2013.01); *A61L 27/3604* (2013.01); *A61L 27/3633* (2013.01); *A61L 27/3641* (2013.01); *A61L 27/507* (2013.01); *A61L 27/54* (2013.01); *A61L 27/58* (2013.01); *A61B 2017/00646* (2013.01); *A61F 2002/8483* (2013.01); *A61F 2210/0076* (2013.01); *A61L 2300/406* (2013.01); *A61L 2300/41* (2013.01); *A61L 2300/414* (2013.01); *A61L 2300/604* (2013.01); *A61L 2400/18* (2013.01); *A61L 2430/20* (2013.01)

(58) Field of Classification Search
None
See application file for complete search history.

(56) References Cited

U.S. PATENT DOCUMENTS 6,569,147 B1 * 5/2003 Evans ............... A61B 17/22
                                                    604/509
8,778,012 B2 * 7/2014 Matheny ............. A61L 27/58
                                                    623/1.36

(Continued)

*Primary Examiner* — Elizabeth C Kemmerer
(74) *Attorney, Agent, or Firm* — Francis Law Group

(57) ABSTRACT

Extracellular matrix (ECM) constructs having a biodegradable support scaffold and an anchoring mechanism, which includes a plurality of biodegradable microneedles that are capable of piercing tissue and anchoring therein. In a preferred embodiment, the support scaffold and anchoring mechanism comprise an ECM material. In some embodiments, the microneedles are also capable of administering a biologically active agent and/or a pharmacological composition to the engaged tissue.

8 Claims, 11 Drawing Sheets

Related U.S. Application Data continuation-in-part of application No. 13/686,131, filed on Nov. 27, 2012, now Pat. No. 8,778,012, and a continuation-in-part of application No. 11/747,028, filed on May 10, 2007, now Pat. No. 9,034,367.

(51) Int. Cl.
*A61L 27/54* (2006.01)
*A61L 27/58* (2006.01)
*A61B 17/00* (2006.01)
*A61F 2/848* (2013.01)

(56) References Cited

U.S. PATENT DOCUMENTS

| | | | | |
|---|---|---|---|---|
| 8,808,363 B2 * | 8/2014 | Perry | ................... | A61F 2/07 606/213 |
| 2001/0041928 A1 * | 11/2001 | Pavcnik | ................... | A61F 2/07 623/1.13 |
| 2002/0082543 A1 * | 6/2002 | Park | ................... | A61B 5/1411 604/21 |

* cited by examiner

EXTRACELLULAR MATRIX CONSTRUCTS FOR TREATING DAMAGED BIOLOGICAL TISSUE

CROSS-REFERENCES TO RELATED APPLICATIONS

This application is a division of U.S. application Ser. No. 14/155,496, filed on Jan. 15, 2014, now U.S. Pat. No. 9,149,496, which is a continuation-in-part of U.S. application Ser. No. 13/686,131, filed on Nov. 27, 2012, now U.S. Pat. No. 8,778,012, which is a continuation-in-part of U.S. application Ser. No. 11/747,028, filed on May 27, 2007, now U.S. Pat. No. 9,034,367.

FIELD OF THE INVENTION

The present invention relates to apparatus and methods for repairing tissue in mammals. More particularly, the present invention relates to extracellular matrix (ECM) constructs for repairing and/or regenerating biological tissue, and closing openings in biological tissue.

BACKGROUND OF THE INVENTION

As is well known in the art, various ECM based apparatus have been developed to regenerate tissue. Illustrative are the ECM based apparatus, i.e. grafts and endografts, disclosed in U.S. Pat. Nos. 7,795,027, 7,910,791, 7,905,826, and 8,025,896 and U.S. application Ser. No. 11/547,348.

The ECM material employed in the noted apparatus will, in most instances, induce host tissue proliferation, bioremodeling, and regeneration of tissue structures.

A major drawback of the noted ECM based apparatus, as well as most known apparatus, is that the means employed to secure the apparatus to tissue often comprise or include a permanent structure that remains in the body, i.e. non-biodegradable. As is well known in the art, such structures (or devices) can, and in most instances will, cause irritation and undesirable biologic responses in the surrounding tissue.

Such structures (and devices) are also prone to failure, resulting in severe adverse consequences, e.g., ruptured vessels.

A further drawback of known ECM apparatus is that the means employed to secure the apparatus to tissue is often ineffective. In the case of an ECM based endograft that is deployed in a cardiovascular vessel, if the endograft is not placed in intimate contact with the vessel wall, blood can, and in most instances will, pool between the endograft and vessel wall. The can result in severe adverse consequences, including vascular thrombosis.

There is thus a need for improved ECM based cardiovascular structures or constructs that employ biocompatible anchoring or securing means that effectively and safely secure cardiovascular structures, such as grafts and vascular prostheses, to biological tissue.

It is therefore an object of the present invention to provide ECM based cardiovascular structures, i.e. ECM constructs, having biocompatible anchoring means that effectively and safely secure the ECM constructs to biological tissue.

It is another object of the present invention to provide ECM constructs having biocompatible and biodegradable anchoring means that effectively and safely secure the ECM constructs to biological tissue, and, while engaged to the tissue, induce host tissue proliferation, bioremodeling and regeneration of new tissue, and tissue structures with site-specific structural and functional properties.

It is another object of the present invention to provide ECM constructs that deliver one or more biologically active agents, such as cells and growth factors, and/or one or more pharmacological or therapeutic agents to biological tissue when engaged thereto.

It is another object of the present invention to provide ECM constructs that can be readily employed to close and maintain closure of an opening in biological tissue, e.g. a surgical incision, and, if desired, also administer one or more biologically active agents and/or one or more pharmacological or therapeutic agents to biological tissue proximate the opening when engaged to the biological tissue.

As will readily be appreciated by one having ordinary skill in the art, the ECM constructs of the invention provide numerous advantages over conventional ECM based and non-ECM based apparatus for repairing and/or regenerating tissue. Among the advantages are the following:

The provision of ECM constructs that employ biocompatible and, in some embodiments, biodegradable anchoring means that effectively and safely secure the ECM constructs to biological tissue for a predetermined period of time;

The provision of ECM constructs that substantially reduce or eliminate (i) the harsh biological responses associated with conventional polymeric and metal ECM based and non-ECM apparatus, and (ii) the formation of inflammation and infection after deployment;

The provision of ECM constructs that can be readily and effectively employed to treat damaged or diseased biological tissue; particularly, cardiovascular tissue;

The provision of ECM constructs that can be readily employed to close and maintain closure of openings in biological tissue;

The provision of ECM constructs that induce host tissue proliferation, bioremodeling and regeneration of new tissue, and tissue structures with site-specific structural and functional properties; and The provision of ECM constructs that effectively administer at least one biologically active agent and/or pharmacological agent or composition to a subject's tissue and, thereby produce a desired biological and/or therapeutic effect.

SUMMARY OF THE INVENTION

The present invention is directed to extracellular matrix (ECM) constructs for repairing and/or regenerating biological tissue.

In some embodiments of the invention, the ECM constructs include a biocompatible support scaffold, more preferably, a biocompatible and biodegradable support scaffold, and an anchoring mechanism.

In some embodiments, the support scaffold and anchoring mechanism comprise separate elements or components.

In some embodiments, the support scaffold and anchoring mechanism comprise an integral element or component, i.e. an integral support scaffold/anchoring mechanism.

In some embodiments, the support scaffolds and anchoring mechanisms and, hence, ECM constructs formed therefrom comprise planar or linear members, e.g., grafts. In some embodiments, the graft support scaffolds comprise an ECM material or composition, i.e. a composition that includes at last one ECM material. In some embodiments, the graft anchoring mechanisms similarly comprise an ECM material or composition.

In some embodiments, the ECM graft constructs include at least one ECM layer, i.e. an ECM sheet or ECM coating, disposed on the top surface of the anchoring member.

In some embodiments of the invention, wherein the ECM graft constructs include an integral support scaffold/microneedle anchoring member, the ECM graft constructs include at least one ECM layer disposed on the top surface of the integral support scaffold/microneedle anchoring member.

In some embodiments, the ECM graft constructs include at least one ECM layer disposed on the top and bottom surfaces of the anchoring mechanism.

In some embodiments of the invention, wherein the ECM graft constructs include an integral support scaffold/microneedle anchoring member, the ECM graft constructs include at least one ECM layer disposed on the top and bottom surfaces of the integral support scaffold/microneedle anchoring member.

In a preferred embodiment of the invention, the ECM material is derived from a mammalian tissue source, which can comprise, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

In some embodiments of the invention, the ECM composition (or material) includes at least one biologically active agent, i.e. an agent that induces or modulates a physiological or biological process, or cellular activity, e.g., induces proliferation, and/or growth and/or regeneration of tissue.

In some embodiments of the invention, the biologically active agent comprises a cell selected from the group comprising, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some embodiments of the invention, the biologically active agent comprises a growth factor selected from the group comprising, without limitation, a platelet derived growth factor (PDGF), epidermal growth factor (EGF), transforming growth factor alpha (TGF-α), transforming growth factor beta (TGF-β), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platlet derived growth factor (PDGF), tumor necrosis factor alpha (TNA-α), and placental growth factor (PLGF).

In some embodiments of the invention, the biologically active agent comprises a protein selected from the group comprising, without limitation, collagen (types I-V), proteoglycans, glycosaminoglycans (GAGs), glycoproteins, cytokines, cell-surface associated proteins, and cell adhesion molecules (CAMs).

In some embodiments of the invention, the ECM composition (or material) includes at least one pharmacological agent or composition, i.e. an agent, drug, compound, composition of matter or mixture thereof, including its formulation, which provides some therapeutic, often beneficial, effect.

In a preferred embodiment, the pharmacological agent or composition is selected from the group comprising, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or antithrombic agents, DNA, RNA, modified DNA and RNA, NSAIDs, and inhibitors of DNA, RNA or protein synthesis.

In a preferred embodiment, the anchoring mechanisms of the invention comprise microneedle anchoring members having a plurality of biocompatible microneedles or barbs that are adapted to pierce tissue and secure the ECM constructs to biological tissue.

In a preferred embodiment, the microneedles comprise biocompatible and biodegradable members.

In some embodiments of the invention, the microneedle anchoring members comprise a biocompatible metal selected from the group comprising, without limitation, stainless steel and magnesium.

In some embodiments, the microneedle anchoring members comprise a polymeric material.

In some embodiments, the microneedles comprise an ECM composition and, hence, facilitate the direct administration of the ECM composition to biological tissue, when the ECM construct is engaged thereto.

In some embodiments, the microneedles comprise agent-eluting members that facilitate the direct delivery of a biologically active agent or pharmacological agent (or composition) to biological tissue, when the ECM construct is engaged thereto.

According to the invention, in some embodiments of the invention, wherein the support mechanism or anchoring mechanism comprises an ECM composition or material, upon placement of an ECM construct on host tissue, e.g., damaged or diseased region of a myocardium or vessel, the ECM composition (or material) and, hence, ECM construct formed therefrom, induces tissue proliferation, bioremodeling, including neovascularization, e.g., vasculogenesis, angiogenesis and intussusceptions, and regeneration of new tissue structures with site-specific structural and functional properties.

In some embodiments of the invention, wherein the support scaffold and/or anchoring mechanism includes a biologically active agent or pharmacological agent (or composition), a desired biological and/or therapeutic action is also effectuated.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1A:
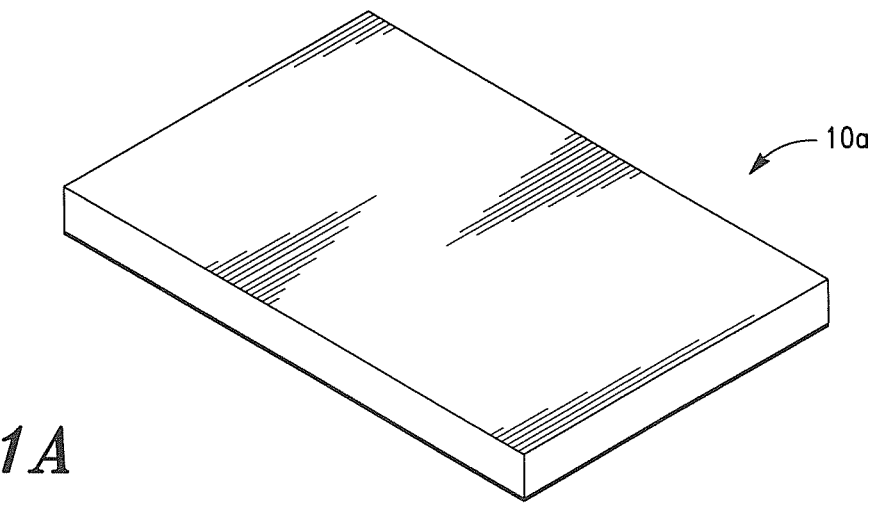
FIGS. 1A-1C are perspective views of several embodiments of planar ECM support scaffolds, in accordance with the invention.

Before describing the present invention in detail, it is to be understood that this invention is not limited to particularly exemplified apparatus, systems, materials, compositions, structures or methods as such may, of course, vary. Thus, although a number of apparatus, systems, materials, compositions, structures and methods similar or equivalent to those described herein can be used in the practice of the present invention, the preferred apparatus, systems, materials, compositions, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "an active" includes two or more such actives and the like.

Further, ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10", as well as "greater than or equal to 10" is also disclosed.

Definitions

The term "graft", as used herein, means and includes a portion of a tissue or organ configured for placement on host tissue to repair and/or regenerate tissue. The term "repair", as used herein, means and includes closure and/or maintaining closure of an opening in biological tissue, e.g., a surgical incision.

The terms "endograft" and "prosthesis" are used interchangeably herein, and mean and include a device or system that is configured for implantation in a lumen or vessel, including, without limitation, stents, i.e. covered and non-covered, and other similar endoluminal support devices.

The term "vessel", as used herein, means and includes any bodily lumen, canal, conduit, duct or passageway, including, but not limited to, blood vessels, bile ducts, the esophagus, the trachea, the ureter and the urethra. A vessel can comprise an existing lumen, canal, conduit, duct or passageway or a lumen, canal, conduit, duct or passageway created by surgical intervention.

The term "biocompatible", as used herein, means a device or material that is substantially non-toxic in an in vivo environment, and is not substantially rejected by a recipient's physiological system, i.e. non-antigenic.

The terms "extracellular matrix", "ECM" and "ECM material" are used interchangeably herein, and mean and include a collagen-rich substance that is found in between cells in mammalian tissue, and any material processed therefrom, e.g. decellularized ECM. According to the invention, the ECM material can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The ECM material can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuceptive angiogenesis, sprouting angiogenesis, therapeutic angiogenesis and vasculogenesis.

The terms "biologically active agent" and "biologically active composition" are used interchangeably herein, and mean and include agent that induces or modulates a physiological or biological process, or cellular activity, e.g., induces proliferation, and/or growth and/or regeneration of tissue.

The terms "biologically active agent" and "biologically active composition" thus mean and include, without limitation, the following growth factors: platelet derived growth factor (PDGF), epidermal growth factor (EGF), transforming growth factor alpha (TGF-α), transforming growth factor beta (TGF-β), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platelet derived growth factor (PDGF), tumor necrosis factor alpha (TNA-α), and placental growth factor (PLGF).

The terms "biologically active agent" and "biologically active composition" also mean and include, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

The terms "biologically active agent" and "biologically active composition" also mean and include, without limitation, the following biologically active agents (referred to interchangeably herein as a "protein", "peptide" and "polypeptide"): collagen (types I-V), proteoglycans, glycosaminoglycans (GAGs), glycoproteins, cytokines, cell-surface associated proteins, cell adhesion molecules (CAM), endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, finulin II, integrins, transmembrane molecules, thrombospondins, ostepontins, and angiotensin converting enzymes (ACE).

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent", "drug" and "active agent formulation" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent", "drug" and "active agent formulation" thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

The terms "pharmacological agent", "active agent", "drug" and "active agent formulation" further mean and include the following Class I-Class V anti-arrhythmic agents: (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent", "drug" and "active agent formulation" further mean and include, without limitation, the following antibiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent", "drug" and "active agent formulation" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent", "active agent", "drug" and "active agent formulation" can further include one or more classes of narcotic analgesics, including, without limitation, morphine, codeine, heroin, hydromorphone, levorphanol, meperidine, methadone, oxycodone, propoxyphene, fentanyl, methadone, naloxone, buprenorphine, butorphanol, nalbuphine and pentazocine.

The terms "pharmacological agent", "active agent", "drug" and "active agent formulation" can further include one or more classes of topical or local anesthetics, including, without limitation, esters, such as benzocaine, chloroprocaine, cocaine, cyclomethycaine, dimethocaine/larocaine, piperocaine, propoxycaine, procaine/novacaine, proparacaine, and tetracaine/amethocaine. Local anesthetics can also include, without limitation, amides, such as articaine, bupivacaine, cinchocaine/dibucaine, etidocaine, levobupivacaine, lidocaine/lignocaine, mepivacaine, prilocaine, ropivacaine, and trimecaine. Local anesthetics can further include combinations of the above from either amides or esters.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, trifiumidate, zidometacin, and zomepirac sodium.

The term "pharmacological composition", as used herein, means and includes a composition comprising a "pharmacological agent" and/or a "biologically active agent" and/or any additional agent or component identified herein.

The term "ECM composition", as used herein, means and includes a composition comprising at least one ECM material.

The term "therapeutically effective", as used herein, means that the amount of the "pharmacological composition" and/or "pharmacological agent" and/or "biologically active agent" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "prevent" and "preventing" are used interchangeably herein, and mean and include reducing the frequency or severity of a disease or condition. The term does not require an absolute preclusion of the disease or condition. Rather, this term includes decreasing the chance for disease occurrence.

The terms "treat" and "treatment" are used interchangeably herein, and mean and include medical management of a patient with the intent to cure, ameliorate, stabilize, or prevent a disease, pathological condition, or disorder. The terms include "active treatment", i.e. treatment directed specifically toward the improvement of a disease, pathological condition, or disorder, and "causal treatment", i.e. treatment directed toward removal of the cause of the associated disease, pathological condition, or disorder.

The terms "treat" and "treatment" further include "palliative treatment", i.e. treatment designed for the relief of symptoms rather than the curing of the disease, pathological condition, or disorder, "preventative treatment", i.e. treatment directed to minimizing or partially or completely inhibiting the development of the associated disease, pathological condition, or disorder, and "supportive treatment", i.e. treatment employed to supplement another specific therapy directed toward the improvement of the associated disease, pathological condition, or disorder.

The terms "optional" and "optionally" mean that the subsequently described event, circumstance, or material may or may not occur or be present, and that the description includes instances where the event, circumstance, or material occurs or is present and instances where it does not occur or is not present.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As discussed above, the present invention is directed to extracellular matrix (ECM) constructs for repairing and/or regenerating biological tissue. As will readily be appreciated by one having ordinary skill in the art, the present invention substantially reduces or eliminates the disadvantages and drawbacks associated with prior art methods and apparatus for repairing damaged or diseased tissue, and closing openings in biological tissue.

According to the invention, in some embodiments of the invention, upon deployment of an ECM construct of the invention to damaged or diseased biological tissue, 'modulated healing" is effectuated.

The term "modulated healing", as used herein, and variants of this language generally refer to the modulation (e.g., alteration, delay, retardation, reduction, etc.) of a process involving different cascades or sequences of naturally occurring tissue repair in response to localized tissue damage or injury, substantially reducing their inflammatory effect. Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments, the ECM constructs of the invention are specifically formulated (or designed) to alter, delay, retard, reduce, and/or detain one or more of the phases associated with healing of damaged tissue, including, but not limited to, the inflammatory phase (e.g., platelet or fibrin deposition), and the proliferative phase.

In some embodiments, "modulated healing" refers to the ability of an ECM construct to alter a substantial inflammatory phase (e.g., platelet or fibrin deposition) at the beginning of the tissue healing process. As used herein, the phrase "alter a substantial inflammatory phase" refers to the ability of an ECM construct to substantially reduce the inflammatory response at an injury site.

In such an instance, a minor amount of inflammation may ensue in response to tissue injury, but this level of inflammation response, e.g., platelet and/or fibrin deposition, is substantially reduced when compared to inflammation that takes place in the absence of an ECM construct of the invention.

For example, the ECM constructs discussed herein have been shown experimentally to delay or alter the inflammatory response associated with damaged tissue, as well as excessive formation of connective fibrous tissue following tissue damage or injury. The ECM constructs have also been shown experimentally to delay or reduce fibrin deposition and platelet attachment to a blood contact surface following tissue damage.

In some embodiments of the invention, "modulated healing" refers to the ability of an ECM construct of the invention to induce host tissue proliferation, bioremodeling, including neovascularization, e.g., vasculogenesis, angiogenesis, and intussusception, and regeneration of tissue structures with site-specific structural and functional properties.

Accordingly, the ECM constructs of the invention provide an excellent means for treating damaged or diseased biologically tissue, including closing and maintaining closure of openings in biological tissue, e.g., closure of openings in tissue after surgical intervention.

As indicated above, in some embodiments of the invention, the ECM constructs include a biocompatible support scaffold, more preferably, a biocompatible and biodegradable support scaffold, and an anchoring mechanism. In some embodiments, the support scaffold and anchoring mechanism comprise separate elements or components. In some embodiments, the support scaffold and anchoring mechanism comprise an integral element or component.

As discussed in detail below, in some embodiments, the support scaffolds and anchoring mechanisms and, hence, ECM constructs formed therefrom comprise planar or linear members, e.g., grafts. In some embodiments, the support scaffolds of the ECM graft constructs comprise an ECM material or composition. In some embodiments, the anchoring mechanisms of the ECM graft constructs similarly comprise an ECM material or composition.

In some embodiments, the ECM constructs of the invention comprise substantially tubular members.

In some embodiments, the ECM graft constructs include at least one ECM layer disposed on the top surface of the anchoring member.

In some embodiments of the invention, wherein the ECM graft constructs include an integral support scaffold/microneedle anchoring member, the ECM graft constructs include at least one ECM layer disposed on the top surface of the integral support scaffold/microneedle anchoring member.

In some embodiments, the ECM graft constructs include at least one ECM layer disposed on the top and bottom surfaces of the anchoring mechanism.

In some embodiments of the invention, wherein the ECM graft constructs include an integral support scaffold/microneedle anchoring member, the ECM graft constructs include at least one ECM layer disposed on the top and bottom surfaces of the integral support scaffold/microneedle anchoring member.

According to the invention, the ECM layers can comprise one or more sheets of ECM material or one or more ECM coatings, i.e. ECM compositions comprising at least one ECM material.

According to the invention, the ECM material can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety.

According to the invention, the ECM material can also be sterilized via applicant's proprietary novasterilis process, as disclosed in Co-Pending U.S. application Ser. No. 13/480,205; which is expressly incorporated herein in their entirety.

In a preferred embodiment, the mammalian tissue sources include, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The ECM material can also be derived from the same or different mammalian tissue sources, as disclosed in Co-Pending application Ser. Nos. 13/033,053 and 13/033,102; which are incorporated by reference herein.

As stated above, in some embodiments of the invention, the ECM compositions and/or materials and, hence, ECM constructs formed therefrom include at least one additional biologically active agent or composition, i.e. an agent that induces or modulates a physiological or biological process, or cellular activity, e.g., induces proliferation, and/or growth and/or regeneration of tissue.

Suitable biologically active agents include any of the aforementioned biologically active agents, including, without limitation, the aforementioned cells, proteins and growth factors.

In some embodiments, the ECM compositions and/or materials and, hence, ECM constructs formed therefrom include at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

Applicant has found that the noted statins exhibit numerous beneficial properties that provide several beneficial biochemical actions or activities. The properties and beneficial actions are set forth in Applicant's Co-Pending application Ser. No. 13/373,569, filed on Sep. 24, 2012 and Ser. No. 13/782,024, filed on Mar. 1, 2013; which are incorporated by reference herein in their entirety.

In some embodiments of the invention, the pharmacological agent comprises chitosan. As also set forth in detail in Co-Pending application Ser. No. 13/573,569, chitosan also exhibits numerous beneficial properties that provide several beneficial biochemical actions or activities.

Additional suitable pharmacological agents and compositions that can be delivered within the scope of the invention are disclosed in Pat. Pub. Nos. 20070014874, 20070014873, 20070014872, 20070014871, 20070014870, 20070014869, and 20070014868; which are expressly incorporated by reference herein in its entirety.

According to the invention, the amount of a pharmacological agent added to an ECM composition or material, and, hence, ECM construct formed therefrom will, of course, vary from agent to agent. For example, in one embodiment, wherein the pharmacological agent comprises diclofenac (Voltaren®), the amount of diclofenac included in the ECM material is preferably in the range of 10 µg-75 mg.

According to the invention, the biologically active and pharmacological agents referenced above can comprise various forms. In some embodiments of the invention, the biologically active and pharmacological agents, e.g. simvastatin and/or chitosan, comprise microcapsules that provide delayed delivery of the agent contained therein.

As indicated above, in some embodiments of the invention, upon deployment of an ECM construct of the invention, modulated healing is effectuated.

Thus, in some embodiments, upon deployment of an ECM construct of the invention, the ECM construct(s) modulates the inflammatory phase (e.g., platelet or fibrin deposition) at the beginning of the tissue healing process.

In some embodiments of the invention, upon deployment of an ECM construct of the invention, regeneration of tissue structures with site-specific structural and functional properties is effectuated.

As stated above, the support scaffolds of the invention preferably comprise a biocompatible material, more preferably, a biocompatible and biodegradable material.

Thus, as set forth in Co-Pending application Ser. No. 13/686,131, which is incorporated by reference herein in its entirety, in some embodiments of the invention, the support scaffolds comprise a biocompatible polymeric material or composition.

According to the invention, the polymeric composition can comprises, without limitation, polyglycolide (PGA), polylactide (PLA), polyepsilon-caprolactone, poly dioxanone (a polyether-ester), poly lactide-co-glycolide, polyamide esters, polyalkalene esters, polyvinyl esters, polyvinyl alcohol, and polyanhydrides. Natural polymeric materials, include, without limitation, polysaccharides (e.g. starch and cellulose), proteins (e.g., gelatin, casein, silk, wool, etc.), and polyesters (e.g., polyhydroxyalkanoates).

As stated above, the ECM constructs of the invention further include an anchoring mechanism. In a preferred embodiment, the anchoring mechanism comprises a microneedle anchoring member having a plurality of biodegradable microneedles or barbs that are adapted to pierce tissue and secure the ECM constructs to biological tissue.

In some embodiments, the microneedles comprise an ECM composition and, hence, facilitate the direct administration of the ECM composition to biological tissue, when the ECM construct is engaged thereto.

As set forth in Co-Pending application Ser. No. 13/686,131, in some embodiments, the microneedles comprise agent-eluting members that facilitate the direct administration of a biologically active agent or pharmacological agent or composition to biological tissue, when the ECM construct is engaged thereto.

According to the invention, in embodiments of the invention, wherein the microneedles (or anchoring mechanism) comprise an ECM composition or material, upon placement of an ECM construct on host tissue, e.g., damaged or diseased region of a myocardium or vessel, the ECM composition or material induces tissue proliferation, bioremodeling, including neovascularization, e.g., vasculogenesis, angiogenesis and intussusceptions, and regeneration of new tissue structures with site-specific structural and functional properties.

In embodiments of the invention, wherein the support scaffold and/or anchoring mechanism of the ECM construct comprise an ECM composition or material that includes a biologically active agent or pharmacological agent or composition, or, as discussed in detail below, the anchoring member comprises a microneedle anchoring member having agent-eluting microneedles that include a biologically active agent or pharmacological agent or composition, upon placement of an ECM construct on host tissue, a desired biological and/or therapeutic action is also effectuated.

In embodiments of the invention, wherein the support scaffold and/or anchoring mechanism of the ECM construct comprise an ECM composition or material, the ECM constructs of the invention are preferably designed and configured to engage biological tissue and maintain contact therewith until remodeling and/or regeneration of new tissue is effectuated. The ECM construct is also preferably designed and configured to degrade after the commencement of new tissue growth.

Figure 1B:
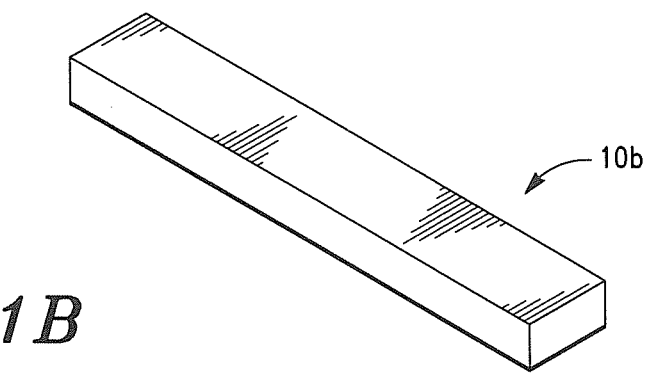
Figure 1C:
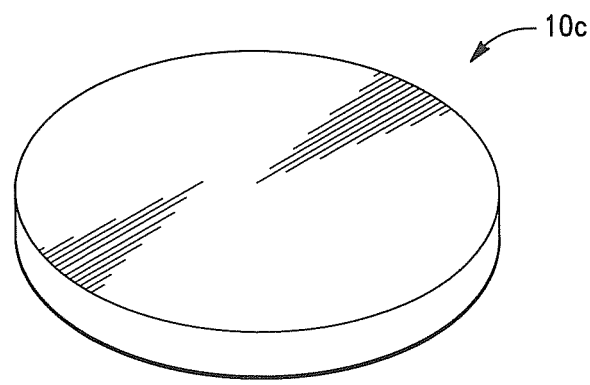

Referring now to FIGS. 1A-1C, there is shown several embodiments of support scaffolds of the invention (denoted generally "10a-10c"). According to the invention and illustrated in FIGS. 1A-1C, the support scaffolds of the invention can comprise various sizes and shapes to facilitate various applications. Thus, as illustrated in FIG. 1B, the support scaffolds can comprise substantially linear elongated members. As illustrated in FIG. 1C, the support scaffolds can also comprise circular shaped members.

According to the invention, the ECM constructs can also be formed with various desired pre-deployment support scaffold surface shapes, e.g. concave or convex, to facilitate contact, preferably, substantially full contact with host tissue.

Figure 2A:
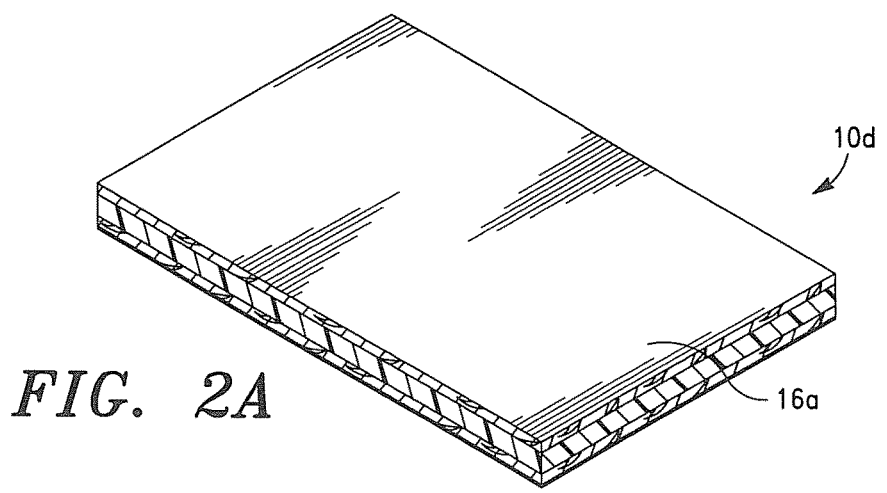
FIG. 2A is a perspective partial sectional view of another embodiment of a planar ECM support scaffold, in accordance with the invention.
Figure 2B:
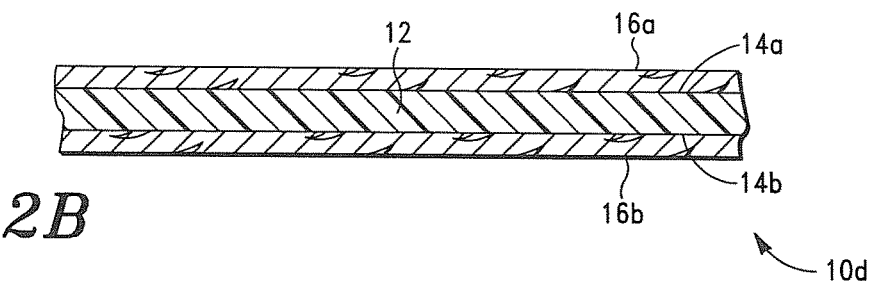
FIG. 2B is a partial front sectional plan view of the support scaffold shown in FIG. 2A, in accordance with the invention.

Referring now to FIGS. 2A and 2B, there is shown another embodiment of a support scaffold of the invention (denoted generally "10d"). As illustrated in FIG. 2A, the support scaffold 10d includes a base member 12, at least a first ECM layer 16a disposed proximate or on the top surface 14a of the scaffold 10d, and at least a second ECM layer 16b disposed proximate or on the bottom surface 14b of the scaffold 10d. The base member 12 is thus encased within the ECM layers 16a, 16b.

Figure 2C:
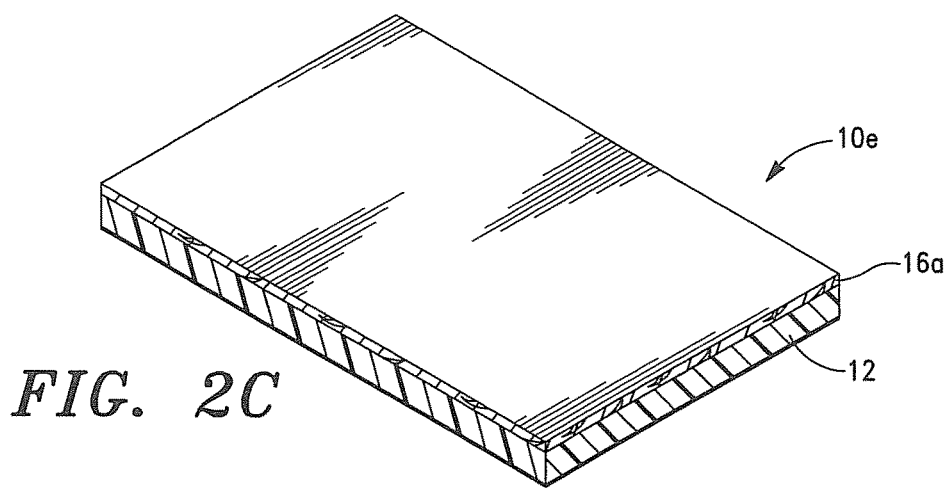
FIG. 2C is a perspective partial sectional view of another embodiment of a planar ECM support scaffold, in accordance with the invention.
Figure 2D:
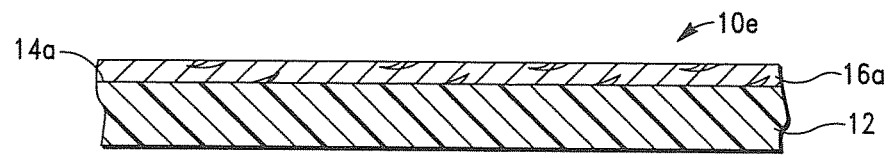
FIG. 2D is a partial front sectional plan view of the support scaffold shown in FIG. 2C, in accordance with the invention.

Referring now to FIGS. 2C and 2D, in some embodiments of the invention, the support scaffold of the invention (denoted generally "10d") includes the base member 12 and only a first ECM layer 16a disposed proximate or on the top surface 14a of the scaffold 10d.

In some embodiments of the invention, the first ECM layer 16a comprises a plurality of ECM sheets, coatings or a combination thereof, i.e. a multi-layer ECM construct. In some embodiments, the first ECM layer 16b comprises a plurality of ECM sheets, coatings or a combination thereof. In some embodiments of the invention, the first and second ECM layers 16a, 16b comprise a plurality of ECM sheets, coatings or a combination thereof.

According to the invention, the ECM sheets and coatings can comprise the same ECM material, e.g. small intestine submucosa (SIS) or different ECM sheets and coatings, e.g. SIS and urinary bladder submucosa (UBS).

Figure 3A:
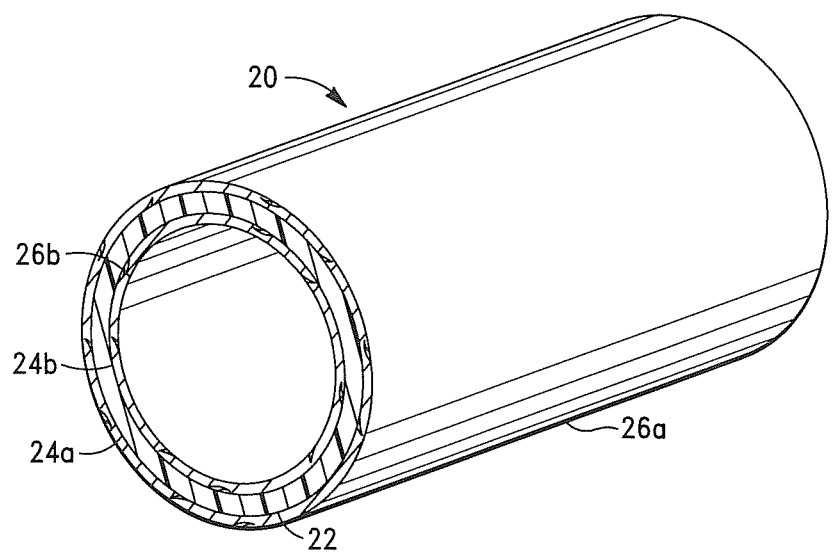
FIG. 3A is a perspective partial sectional view of one embodiment of a tubular ECM support scaffolds, in accordance with the invention.
Figure 3B:
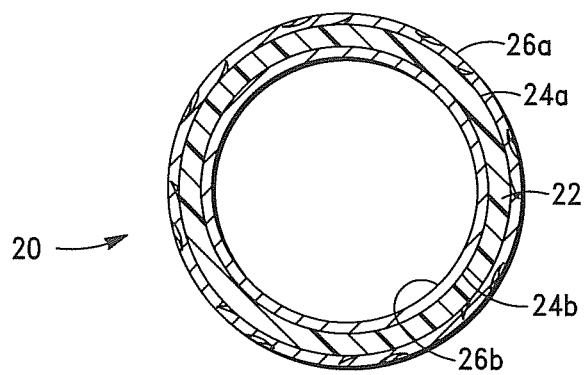
FIG. 3B is a end sectional plan view of the support scaffold shown in FIG. 3A, in accordance with the invention.

Referring now to FIGS. 3A and 3B, there is shown an embodiment of a tubular support scaffold of the invention. As illustrated in FIG. 3A, the support scaffold (denoted generally "20") similarly includes a base member 22, at least a first ECM layer 26a disposed proximate or on the top surface 24a of the scaffold 22, and at least a second ECM layer 26b disposed proximate or on the bottom surface 24b of the scaffold 22.

According to the invention, the first or second ECM layers 26a, 26b can similarly comprise a plurality of wrapped ECM sheets, coatings or a combination thereof.

According to the invention, the ECM sheet layers 16a, 16b, 26a and 26b can be secured to the supports scaffolds 10d, 10e and 22 by any conventional means, e.g., laminating ends, stitching ends, etc.

According to the invention, the ECM layers 16a, 16b, 26a and 26b and coatings can similarly comprise the same ECM material, e.g. small intestine submucosa (SIS) or different ECM sheets and coatings, e.g. SIS and urinary bladder submucosa (UBS).

As indicated above, in a preferred embodiment, the ECM constructs of the invention also include an anchoring mechanism. As also indicated above, in a preferred embodiment, the anchoring mechanisms comprise microneedle anchoring members.

In a preferred embodiment, the microneedle anchoring members include at least one, more preferably, a plurality of biodegradable microneedles or barbs that are adapted to pierce tissue and secure the ECM constructs to biological tissue, e.g. host tissue of a heart or vascular structure.

According to the invention, various shaped microneedles or barbs can be employed within the scope of the invention; provided, the microneedle or barb has a head (or head region) that is able to pierce tissue and maintain engaged to the tissue for a predetermined period of time.

In some embodiments of the invention, the biodegradable microneedles are adapted to secure an ECM construct to tissue for a predetermined engagement period of time within the process of new tissue regeneration.

In some embodiments of the invention, the predetermined engagement period of time is within the range of approximately 12-36 months. In some embodiments, the engagement period of time is within the range of approximately 3-12 months. In some embodiments, the engagement period of time is within the range of approximately 1-3 months.

Thus, in some embodiments, wherein the support scaffold or anchoring mechanism of the ECM construct comprises an ECM composition or material, when the ECM construct engages host biological tissue, e.g. myocardium tissue, the microneedles preferably remain engaged to the host tissue long enough to allow blood vessels to begin to grow. Once blood vessels begin to grow into the ECM construct, e.g., support scaffold or ECM composition disposed on the anchoring mechanism, and stem cells attach to the surface, an endothelium surface grows across the ECM construct and starts to remodel into healthy, native vascular wall cells and, thereby, remodeled tissue.

According to the invention, various microneedles can be employed within the scope of the invention. Several suitable embodiments of tissue piercing microneedles are shown and described in detail in Co-Pending application Ser. No. 13/686,131.

It is, however, understood that the microneedles shown and discussed in Co-Pending application Ser. No. 13/686, 131 are merely exemplar microneedles that can be employed within the scope of the invention and, hence, do not limit the scope of the invention in any manner. Indeed, as stated above, various other shaped microneedles can be employed within the scope of the invention; provided, the microneedle has a head (or head region) that is able to pierce tissue and maintain engaged to the tissue for a predetermined period of time.

According to the invention, the microneedles and, hence, microneedle anchoring members associated therewith can comprise various materials. Preferably, the microneedles and, hence, microneedle anchoring members comprise a biocompatible material, more preferably, a biocompatible and biodegradable material.

In some embodiments of the invention, the microneedles and/or microneedle anchoring members comprise a biocompatible metal, including, without limitation, stainless steel and magnesium.

In some embodiments of the invention, the microneedles and/or microneedle anchoring members comprise one of the aforementioned biocompatible polymeric materials.

In some embodiments of the invention, the microneedles and/or microneedle anchoring members comprise an ECM composition or material.

In some embodiments, the microneedles of the invention comprise agent-eluting members, i.e. structures that facilitate the direct administration of at least one biologically active or pharmacological agent or composition to biological tissue, when an ECM construct of the invention is engaged thereto.

According to the invention, the biologically active or pharmacological agent or composition can comprise any of the aforementioned biologically active and pharmacological agents and compositions, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, statins, compounds that modulate cell migration, cells, proteins, growth factors and other agents and compounds that modulate proliferation and growth of tissue, and vasodilating agents.

In some embodiments of the invention, the agent-eluting capability is facilitated by forming the microneedle(s) out of an ECM composition that includes an additional biologically active agent, e.g. a growth factor, or pharmacologically active agent, e.g. a statin.

In some embodiments of the invention, the agent-eluting capability is facilitated by forming the microneedle(s) out of a pharmacological composition, whereby upon engagement of a biodegradable microneedle to a recipient's tissue, the microneedle dissolves or degrades and the pharmacological composition is administered to the recipient at the engagement site.

In some embodiments, the agent-eluting capability is facilitated by coating the microneedle(s) with a biologically active agent or pharmacological composition, whereby upon engagement of a microneedle to a recipient's tissue, the biologically active agent or pharmacological composition is absorbed and, hence, administered to the recipient at the engagement site.

As set forth in Co-Pending application Ser. No. 13/686, 131, in some embodiments of the invention, the agent-eluting capability is facilitated by providing the microneedle(s) with an internal reservoir that is adapted to receive and contain a biologically active agent or pharmacological composition therein. According to the invention, upon engagement of the noted agent-eluting microneedles to a recipient's tissue, the microneedles dissolve or degrade and the biologically active agent or pharmacological composition contained in the reservoir is administered to the recipient at the engagement site.

As also set forth in Co-Pending application Ser. No. 13/686,131, in some embodiments, the agent-eluting microneedles include at least one, more preferably, a plurality of lumens in communication with the internal reservoir and, hence, biologically active agent or pharmacological composition contained therein. The agent-eluting microneedles further include a biodegradable or bioabsorbable coating (or sealing layer) on the outer surface to temporarily seal the internal reservoir and inter-connected lumens.

According to the invention, upon engagement of the agent-eluting microneedles to a recipient's tissue, the outer coating dissolves or degrades and the biologically active agent or pharmacological composition contained in the reservoir flows out of the lumens and is administered to the recipient's tissue at the engagement site.

Figure 4A:
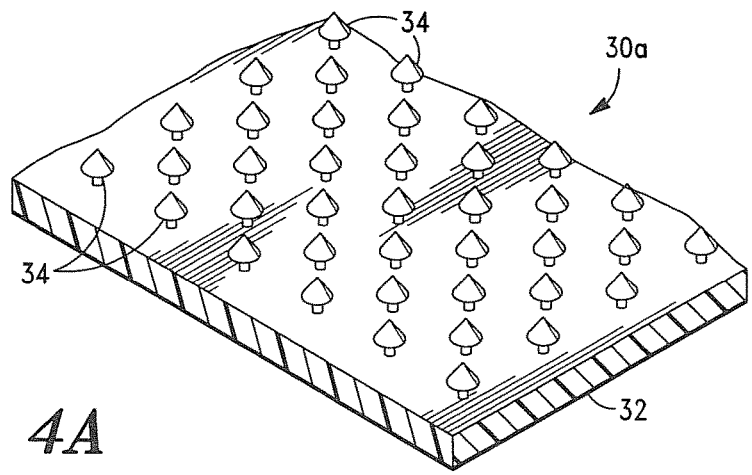
FIG. 4A is a perspective partial sectional view of one embodiment of an ECM construct having an integral support scaffold/microneedle anchoring member, in accordance with the invention.
Figure 4B:
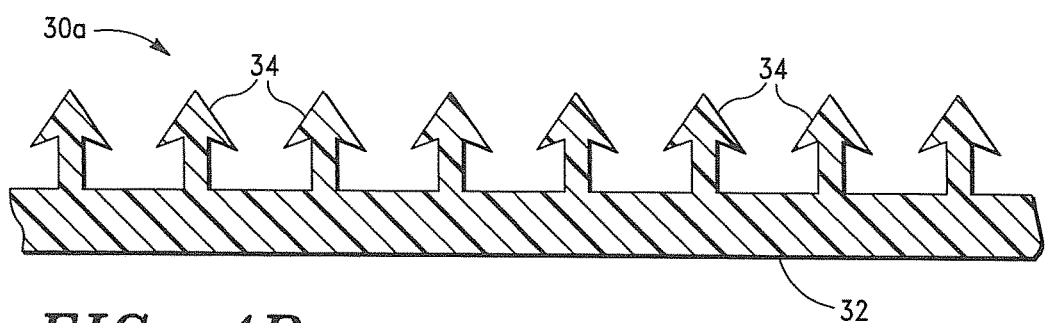
FIG. 4B is a front sectional plan view of the ECM construct shown in FIG. 4A, in accordance with the invention.
Figure 4C:
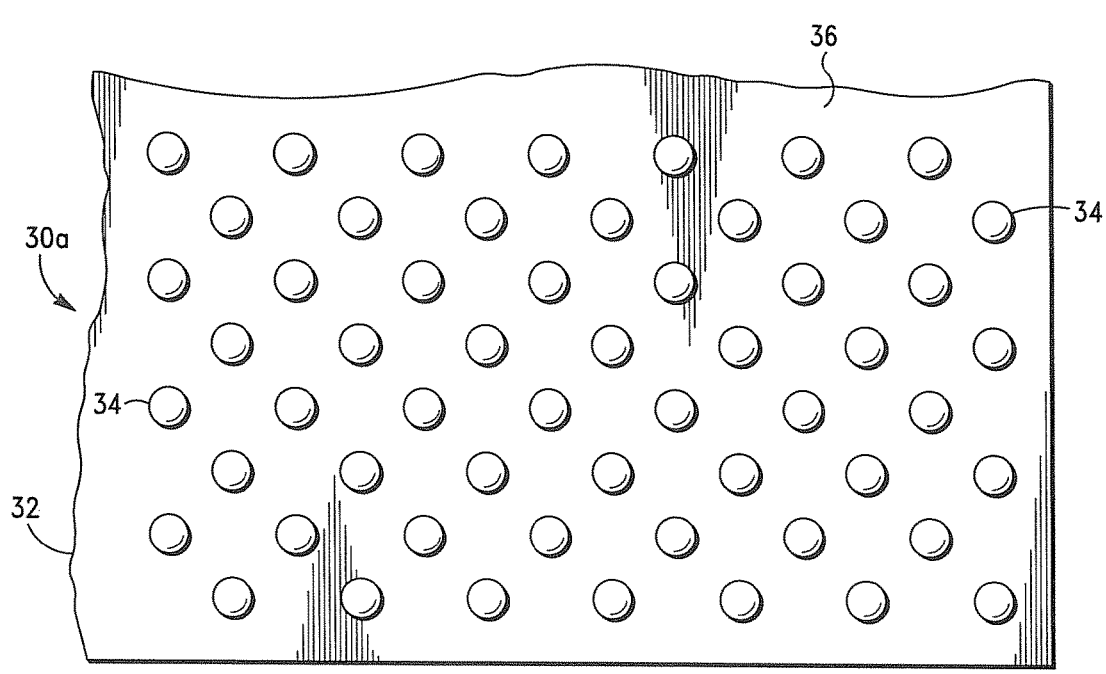
FIG. 4C is a top plan view of the ECM construct shown in FIG. 4A, in accordance with the invention.

Referring now to FIGS. 4A-4C, there is shown one embodiment of an ECM construct of the invention. As illustrated in FIG. 4A, the construct 30a comprises an integral support scaffold/anchoring mechanism 32 having a plurality of microneedles 34.

In a preferred embodiment, the ECM construct 30a comprises an ECM composition. According to the invention, the ECM composition can include one of the aforementioned biologically active agents and/or one of the aforementioned pharmacological agents or compositions.

In some embodiments of the invention, at least the microneedles 34 further include one of the aforementioned ECM layers, i.e. coatings.

According to the invention, the ECM construct 30a can be formed by various conventional means, e.g. molded ECM structure.

Figure 5A:
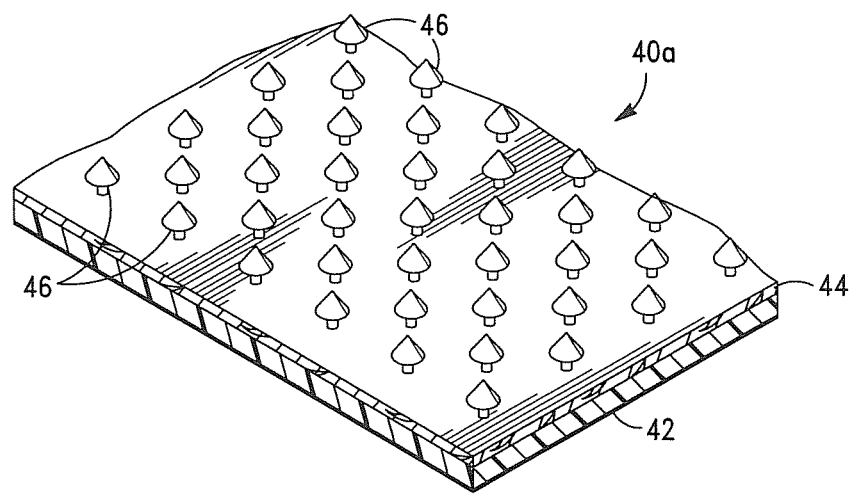
FIG. 5A is a perspective partial sectional view of another embodiment of an ECM construct having an ECM layer disposed thereon, in accordance with the invention.
Figure 5B:
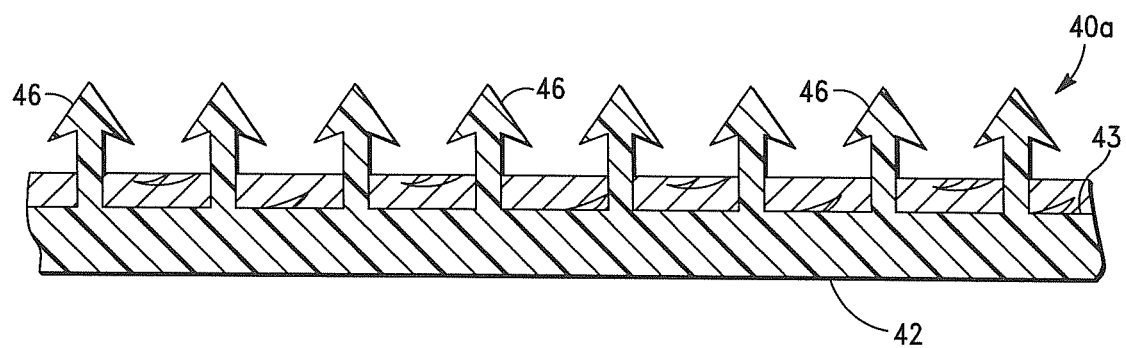
FIG. 5B is a partial front sectional plan view of the ECM construct shown in FIG. 5A, in accordance with the invention.

Referring now to FIGS. 5A and 5B, there is shown another embodiment of an ECM construct of the invention. As illustrated in FIG. 5A, the construct 40a includes a support scaffold 42 that includes a plurality of microneedles 46, and at least one ECM layer 44 that is disposed proximate or on the top surface 43 of the support scaffold 42. According to the invention, the ECM layer 44 can comprise any of the aforementioned ECM layers, e.g. plurality of ECM sheets or coatings.

In some embodiments of the invention, the support scaffold 42 comprises one of the aforementioned metals, e.g. magnesium. In some embodiments, the support scaffold 42 comprises one of the aforementioned polymeric materials.

In some embodiments, the microneedles 46 further include one of the aforementioned ECM compositions. In some embodiments, the microneedles 46 further include a coating comprising a biologically active agent composition or pharmacological composition.

In some embodiments, the top surface 43 of the support scaffold 42 includes one of the aforementioned ECM coatings. In some embodiments, the top surface 43 of the support scaffold 42 includes a coating comprising a biologically active agent composition or pharmacological composition.

As indicated above, in embodiments of the invention, wherein the support mechanism or anchoring mechanism comprises an ECM composition or material, upon placement of an ECM construct on host tissue, e.g., damaged or diseased region of a myocardium or vessel, the ECM composition (or material) and, hence, ECM construct formed therefrom, induces tissue proliferation, bioremodeling, including neovascularization, e.g., vasculogenesis, angiogenesis and intussusceptions, and regeneration of new tissue structures with site-specific structural and functional properties.

In embodiments of the invention, wherein the support scaffold and/or anchoring mechanism includes a biologically active agent or pharmacological agent (or composition) or the anchoring mechanism includes agent-eluting microneedles having one or more biologically active agents or pharmacological agents (or compositions) therein, upon placement of an ECM construct on the host tissue a desired biological and/or therapeutic action is also effectuated.

The ECM constructs can thus be readily employed to treat damaged or diseased biological tissue; particularly, cardiovascular tissue.

Figure 6:
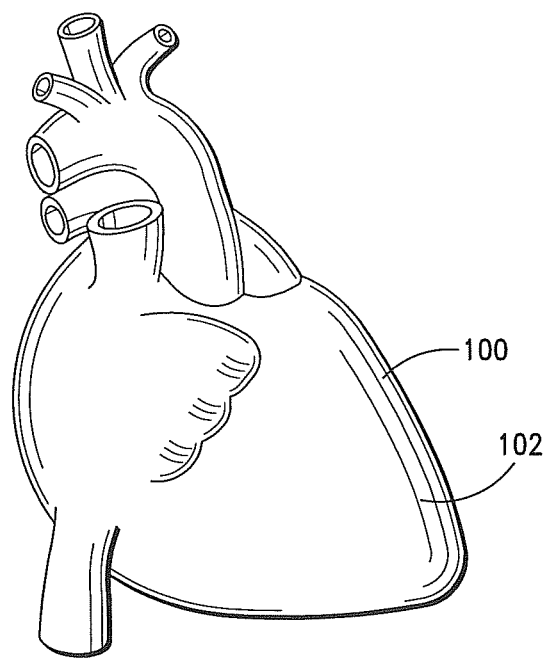
FIG. 6 is a schematic illustration of a human heart.

Referring now to FIG. 6 there is shown a depiction of a normal heart 100. As is well known in the art, the heart wall 102 consists of an inner layer of simple squamous epithelium, referred to as the endocardium. The endocardium overlays the myocardium (a variably thick heart muscle) and is enveloped within a multi-layer tissue structure referred to as the pericardium. The innermost layer of the pericardium, referred to as the visceral pericardium or epicardium, covers the myocardium. An outermost layer of the pericardium, referred to as the fibrous pericardium, attaches the parietal pericardium to the sternum, the great vessels and the diaphragm.

Figure 7:
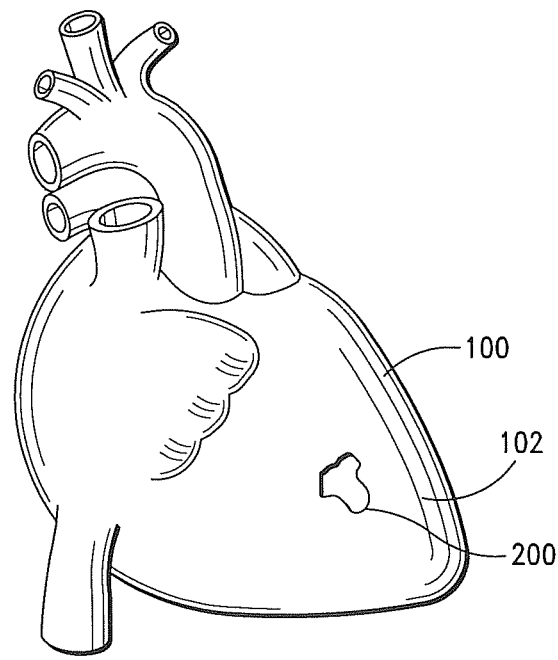
FIG. 7 is a schematic illustration of the human heart shown in FIG. 6 having an infarct region.
Figure 8:
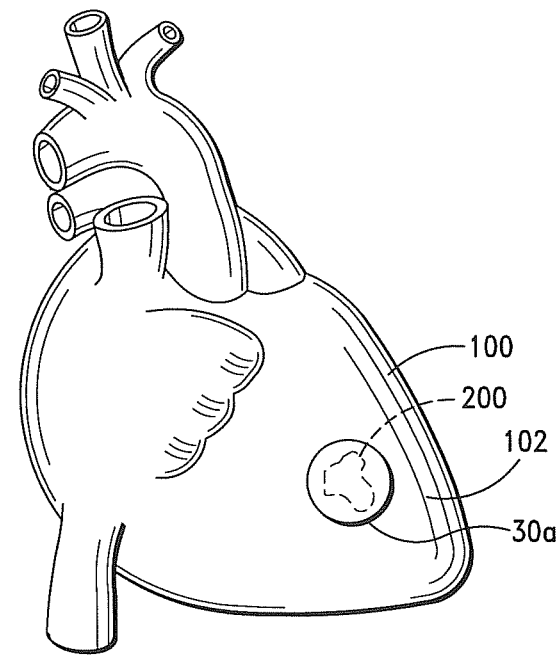
FIG. 8 is a schematic illustration of the human heart shown in FIG. 7 having an ECM construct disposed over the infarct region, in accordance with the invention.

Referring now to FIG. 7, there is shown a depiction of the heart 100 with damaged tissue, i.e. an ischemic infracted region 200. According to the invention, the infarcted region 200 can be effectively treated by disposing an ECM construct of the invention, e.g., ECM construct 30a, proximate, more preferably, directly over the infarcted region 200, as shown in FIG. 8.

As indicated above, the ECM constructs of the invention can also be readily employed to close openings in biological tissue; openings resulting from tissue damage or disease and/or openings resulting from surgical intervention.

Figure 9:
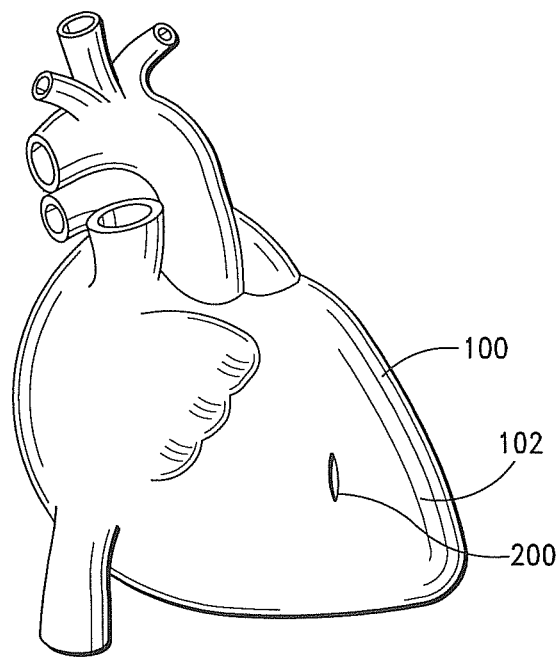
FIG. 9 is a schematic illustration of the human heart shown in FIG. 6 having a surgical incision in the myocardium.
Figure 10:
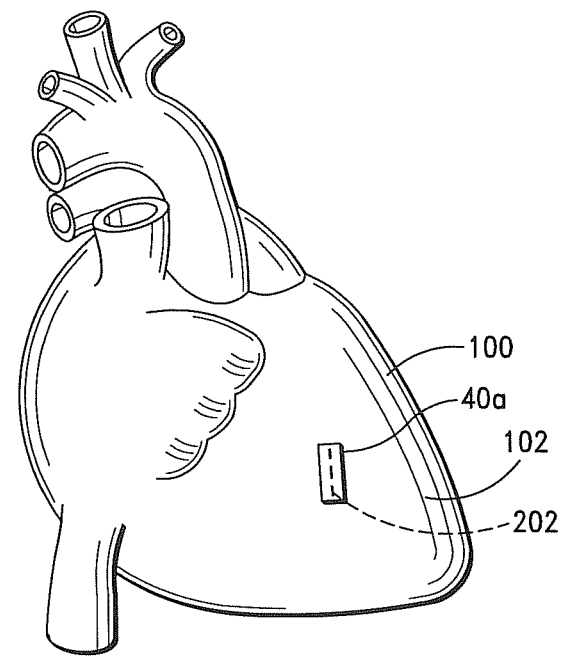
FIG. 10 is a schematic illustration of the human heart shown in FIG. 9 having an ECM construct disposed over the surgical incision, in accordance with the invention.

Referring now to FIG. 9, there is shown a depiction of the heart 100 with a surgical incision 202. Referring now to FIG. 10, there is shown an ECM construct of the invention, e.g. ECM construct 40a, that is disposed over the "now closed" incision 202. As indicated above, in addition to effectively securing closure of the incision 202, if the ECM construct 40a includes a biologically active agent or pharmacological agent (or composition), upon placement of the ECM construct 40a proximate the incision 202 a desired biological and/or therapeutic action is also effectuated.

Figure 11A:
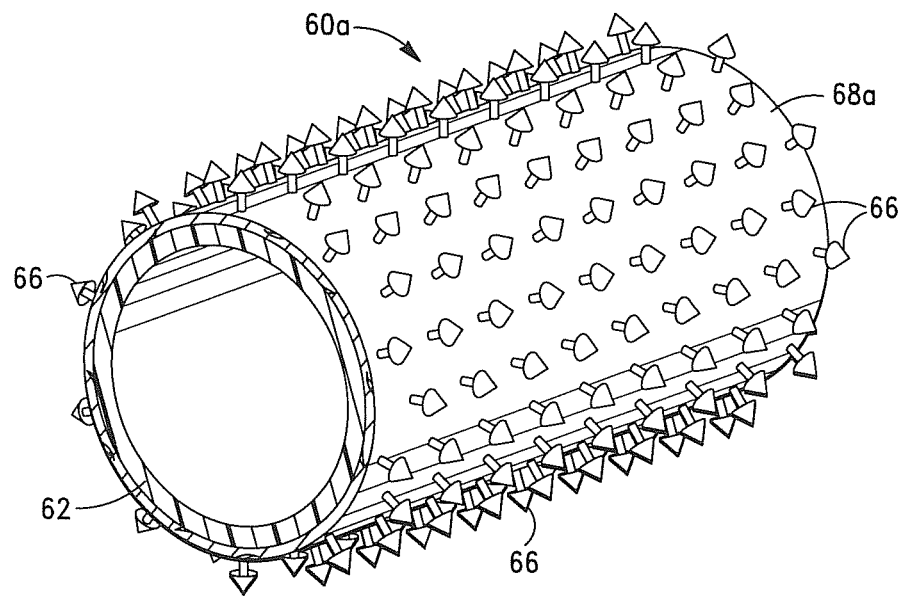
FIG. 11A is a perspective partial sectional view of a tubular embodiment of an ECM construct having a microneedle anchoring member, in accordance with the invention.
Figure 11B:
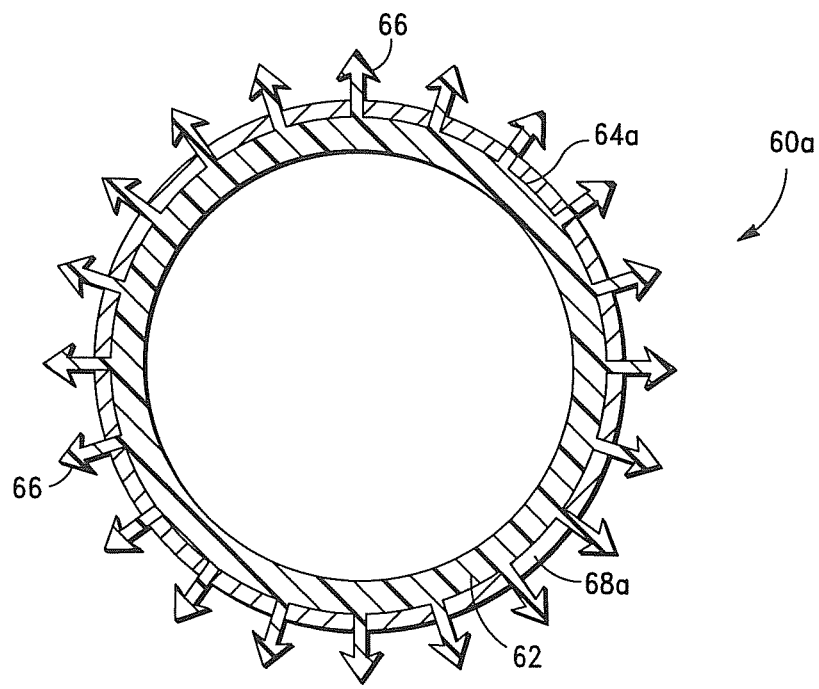
FIG. 11B is a side (or end) sectional plan view of the ECM construct shown in FIG. 11A, in accordance with the invention.

Referring now to FIGS. 11A-11B, there is shown an embodiment of an ECM construct 60a of the invention having a tubular shape to facilitate deployment in a lumen or vessel in the body, e.g., a cardiovascular vessel. As illustrated in FIG. 11A, the construct 60a includes an ECM layer 68a disposed proximate or on the top surface 64a of the construct 60a and an integral support scaffold/microneedle anchoring member 62. The support scaffold/microneedle anchoring member 62 similarly includes a plurality of microneedles 66 that preferably extend through and project out of the ECM layer 68a.

Figure 12:
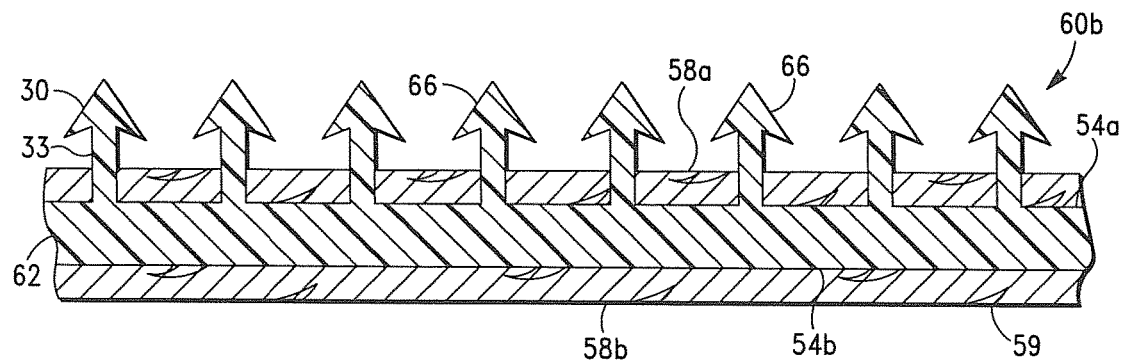
FIG. 12 is a partial front sectional plan view of another embodiment of an ECM construct, in accordance with the invention.
Figure 13:
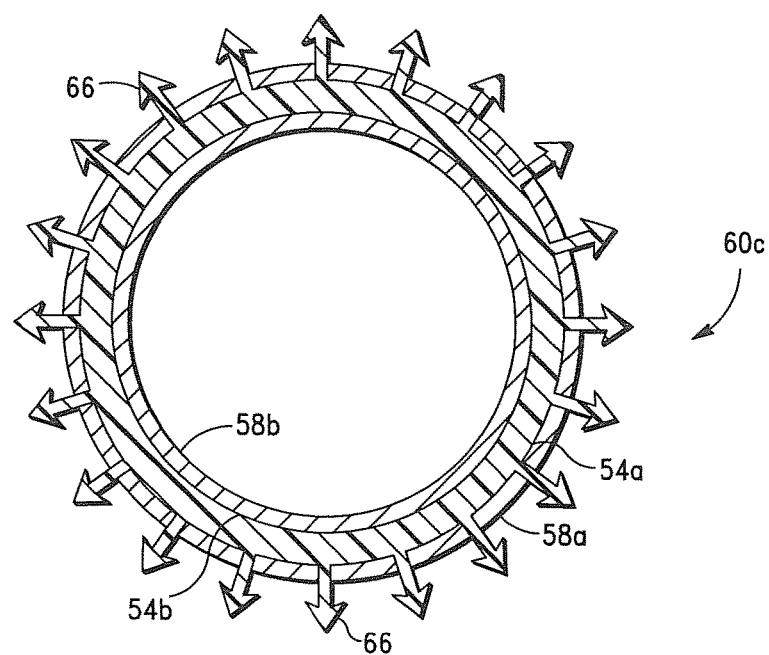
FIG. 13 is a side sectional plan view of another embodiment of a tubular ECM construct, in accordance with the invention.

Referring now to FIGS. 12 and 13, in some embodiments of the invention, the planar and tubular ECM constructs (denoted "60b" and "60c", respectively) include at least a first ECM layer 58a that is disposed proximate to or on the top surface 54a of the integral support scaffold/microneedle anchoring member 62.

In some embodiments, ECM constructs 60a, 60b further include a second ECM layer 58b that is disposed proximate or on the bottom surface 54b of the integral support scaffold/microneedle anchoring member 62.

According to the invention, the ECM layers 58a, 58b can similarly comprise single or multiple sheets of ECM material or one or more ECM coatings.

Figure 14:
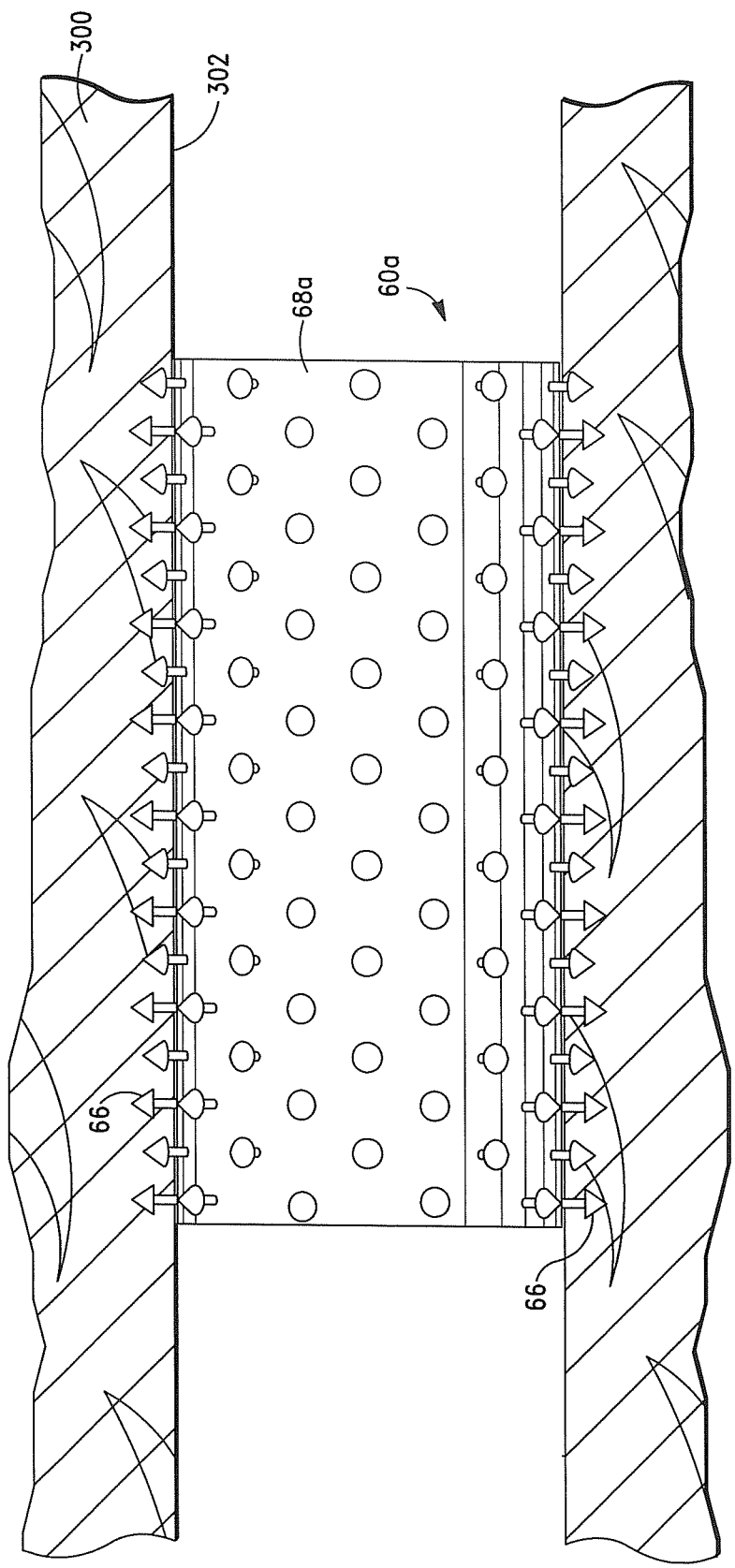
FIG. 14 is a front partial sectional plan view of the ECM construct shown in FIG. 13 engaged to tissue in a cardiovascular vessel, in accordance with the invention.

Referring now to FIG. 14, there is shown an illustration of tubular ECM construct 60a engaged to tissue in a cardiovascular vessel 300. According to the invention, when the construct (or prosthesis) 60a is deployed in the vessel 300 the microneedles 66 pierce the vessel wall 302 and secure the prosthesis 60a to the vessel tissue.

As indicated above, upon engagement of the ECM construct 60a to the vessel wall 302, the ECM construct 30a induces tissue proliferation, bioremodeling, and regeneration of new tissue structures with site-specific structural and functional properties.

As also indicated above, when the ECM construct 60a includes a biologically active agent and/or a pharmacological agent or composition, a desired biological and/or therapeutic action is also effectuated.

One having ordinary skill in the art will thus readily appreciate that the ECM constructs of the invention provide numerous advantages over conventional ECM based and non-ECM based apparatus for repairing and/or regenerating tissue. Among the advantages are the following:

The provision of ECM constructs that can be readily and effectively employed to treat damaged or diseased biological tissue; particularly, cardiovascular tissue;

The provision of ECM constructs that can be readily employed to close and maintain closure of openings in biological tissue;

The provision of ECM constructs that induce host tissue proliferation, bioremodeling and regeneration of new tissue, and tissue structures with site-specific structural and functional properties;

The provision of ECM constructs that substantially reduce or eliminate (i) the harsh biological responses associated with conventional polymeric and metal ECM based and non-ECM apparatus, and (ii) the formation of inflammation and infection after deployment;

The provision of ECM constructs that employ biocompatible and, in some embodiments, biodegradable securing means that effectively and safely secure the ECM constructs to tissue for a predetermined period of time;

The provision of ECM constructs that effectively administer at least one biologically active agent and/or pharmacological agent or composition to a subject's tissue and, thereby produce a desired biological and/or therapeutic effect.

A further advantage of the ECM constructs of the invention is that they can be readily employed in various medical procedures, including, without limitation, treatment of coronary and peripheral vascular disease (PVD) in cardiovascular vessels, including, but not limited to, iliacs, superficial femoral artery, renal artery, tibial artery, popliteal artery, etc., deep vein thromboses (DVT), vascular bypasses, and coronary vascular repair.

The ECM constructs of the invention of the invention can also be readily incorporated in or employed with various cardiovascular conduits, valves and grafts, including, without limitation, the heart valves, conduits and grafts disclosed in U.S. Pat. No. 7,998,196 and U.S. application Ser. No. 13/782,024, filed Mar. 1, 2013, Ser. No. 13/782,289, filed Mar. 1, 2013, Ser. No. 13/804,683, filed Mar. 14, 2013 and Ser. No. 13/328,287, filed Dec. 16, 2011.

The scaffolds and/or microneedles of the invention can also be employed with various additional vascular prostheses, including covered and non-covered stents.

It is understood that the noted applications of the ECM constructs are merely exemplary and, thus, do not limit the scope of the possible applications and, hence, invention.

Without departing from the spirit and scope of this invention, one of ordinary skill can make various changes and modifications to the invention to adapt it to various usages and conditions. As such, these changes and modifications are properly, equitably, and intended to be, within the full range of equivalence of any issued claims.

What is claimed is:

1. An extracellular matrix (ECM) construct for tissue repair, comprising:
a biodegradable and bioremodelable support scaffold; and
a biodegradable and bioremodelable microneedle anchoring member having a top and bottom surface, said microneedle anchoring member including a plurality of biodegradable microneedles that are configured to pierce tissue and anchor therein, said plurality of biodegradable microneedles projecting from at least said microneedle anchoring member top surface,
said biodegradable and bioremodelable support scaffold and anchoring member comprising acellular urinary bladder submucosa, wherein, when said ECM construct is in communication with host tissue, said microneedle anchoring member secures said ECM construct to said host tissue for an engagement period of time in the range of at least 1-3 months, wherein said ECM construct biodegrades and is at least partially remodeled by said host tissue.

2. The ECM construct or claim 1, wherein said biodegradable and bioremodelable support scaffold and microneedle anchoring members comprise an integral member.

3. The ECM construct of claim 1, wherein said acellular urinary bladder submucosa comprises at least one supplemental biologically active agent.

4. The ECM construct of claim 3, wherein said supplemental biologically active agent comprises a basic fibroblast growth factor (bFGF).

5. The ECM construct of claim 1, wherein said acellular urinary bladder submucosa comprises at least one pharmacological agent.

6. The ECM construct of claim 5, wherein said pharmacological agent comprises an anti-inflammatory agent.

7. The ECM construct of claim 5, wherein said pharmacological agent comprises an antibiotic.

8. The ECM construct of claim 5, wherein said pharmacological agent comprises a statin.

* * * * *